US010227284B2

(12) United States Patent
Krill et al.

(10) Patent No.: US 10,227,284 B2
(45) Date of Patent: Mar. 12, 2019

(54) METHOD FOR PREPARING ALPHA-HYDROXYCARBOXYLIC ACID ESTERS IN WHICH AMMONIA IS RECYCLED

(71) Applicant: Evonik Roehm GmbH, Darmstadt (DE)

(72) Inventors: Steffen Krill, Muehltal (DE); Belaid Ait Aissa, Darmstadt (DE); Alexander May, Seeheim-Jugenheim (DE); Marcel Treskow, Darmstadt (DE)

(73) Assignee: Evonik Roehm GmbH, Darmstadt (DE)

(*) Notice: Subject to any disclaimer, the term of this patent is extended or adjusted under 35 U.S.C. 154(b) by 0 days.

(21) Appl. No.: 15/508,200

(22) PCT Filed: Sep. 4, 2015

(86) PCT No.: PCT/EP2015/070196
§ 371 (c)(1),
(2) Date: Mar. 2, 2017

(87) PCT Pub. No.: WO2016/037928
PCT Pub. Date: Mar. 17, 2016

(65) Prior Publication Data
US 2017/0283364 A1    Oct. 5, 2017

(30) Foreign Application Priority Data

Sep. 10, 2014 (EP) .................... 14184249

(51) Int. Cl.
*C07C 67/20* (2006.01)
*B01J 20/20* (2006.01)
*C01C 1/02* (2006.01)
*C01C 3/02* (2006.01)

(52) U.S. Cl.
CPC .............. *C07C 67/20* (2013.01); *B01J 20/20* (2013.01); *C01C 1/024* (2013.01); *C01C 3/0212* (2013.01); *C01C 3/0208* (2013.01)

(58) Field of Classification Search
None
See application file for complete search history.

(56) References Cited

U.S. PATENT DOCUMENTS 6,075,162 A    6/2000  Kida
6,096,173 A    8/2000  Von Hippel et al.
7,423,173 B2   9/2008  Krill et al.
8,569,539 B2  10/2013  May et al.
8,975,440 B2   3/2015  May et al.
9,428,437 B2   8/2016  May et al.
2009/0209781 A1  8/2009  Ackermann et al.

FOREIGN PATENT DOCUMENTS

| DE | 10 2013 213 699 A1 | 1/2015 |
| EP | 0 922 674 A1 | 6/1999 |
| EP | 0 941 984 A2 | 9/1999 |
| EP | 0 941 984 A3 | 9/1999 |
| EP | 0 945 423 B1 | 5/2003 |
| EP | 2 018 362 A1 | 1/2009 |
| EP | 2 415 750 A1 | 2/2012 |
| JP | 6-345692 A | 12/1994 |
| WO | WO 2007/131829 A1 | 11/2007 |
| WO | 2008/009503 A1 | 1/2008 |
| WO | WO 2013/026603 A1 | 2/2013 |

OTHER PUBLICATIONS

Of Turk et al. "Activated Carbon Systems for Removal of Light Gases" 1992, 221-228.*
U.S. Appl. No. 14/129,811, filed Dec. 27, 2013, US 2014-0135521 A1, Koestner, et al.
U.S. Appl. No. 15/323,888, filed Jan. 4, 2017, US 2017-0144960 A1, Krill, et al.
U.S. Appl. No. 15/316,685, filed Dec. 6, 2016, Aissa.
U.S. Appl. No. 14/900,403, filed Dec. 21, 2015, US 2016-0137583 A1, Krill, et al.
U.S. Appl. No. 15/127,937, filed Sep. 21, 2016, US 2017-0101322 A1, May, et al.
International Search Report dated Nov. 4, 2015 in PCT/EP2015/070196 filed Sep. 4, 2015.
European Search Report dated Feb. 25, 2015 in European Application 14184249.2 filed Sep. 10, 2014.
Klaus Weissermel, et al. "Industrial Organic Chemistry", 4th edition Sohio-Process, 2003, pp. 306-309 with cover pages.
Hans-Jörg Bart, et al. "Adsorption", Ullmann's Encyclopedia of Industrial Chemistry, vol. 1, 2012, pp. 549-620.
Ernst Gail, et al. "Cyano Compounds, Inorganic", Ullmann's Encyclopedia of Industrial Chemistry, 5th Edition on CD ROM, vol. 10, 2012, pp. 673-710.

* cited by examiner

Primary Examiner — Ana Z Muresan
(74) Attorney, Agent, or Firm — Gruneberg and Myers PLLC

(57) ABSTRACT

The present invention relates to a process for preparing alpha-hydroxycarboxylic esters proceeding from hydrogen cyanide, wherein the ammonia formed in the step of alcoholysis of the corresponding alpha-hydroxycarboxamide is recycled into a hydrogen cyanide preparation process after a purification step.

11 Claims, 1 Drawing Sheet

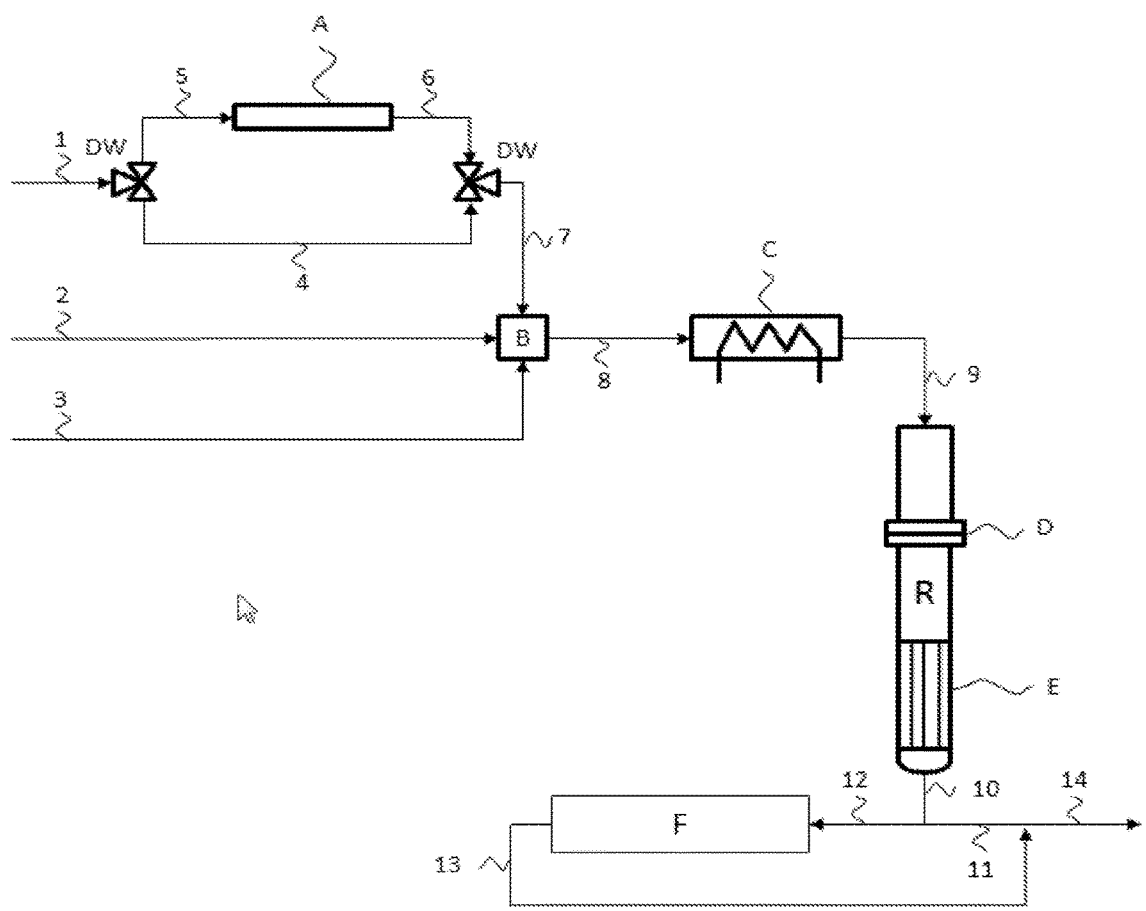

METHOD FOR PREPARING ALPHA-HYDROXYCARBOXYLIC ACID ESTERS IN WHICH AMMONIA IS RECYCLED

FIELD OF THE INVENTION

The present invention relates to a process for preparing alpha-hydroxycarboxylic esters (HCEs) proceeding from hydrogen cyanide, wherein the ammonia formed in the step of alcoholysis of the corresponding alpha-hydroxycarboxamide (HCA) is recycled into a hydrogen cyanide preparation process after a purification step.

BACKGROUND OF THE INVENTION

The preparation of HCEs is sufficiently well known from the prior art. More particularly, the applications EP 2018362 and WO 2013/026603 describe corresponding processes wherein the alcoholysis is effected in the liquid phase under pressure and ammonia formed is distilled off at pressures greater than 1 bar, or the HCE formed is removed via the gas phase.

However, the major problem with this prior art, or else in known processes in which said alcoholysis is effected in the gas phase, is that the isolated ammonia, when recycled into the hydrogen cyanide preparation process, results in considerable losses of catalyst activity even within a short time and makes it impossible to operate the plant economically.

SUMMARY OF THE INVENTION

The problem addressed by present invention is therefore that of processing the ammonia obtained from the preparation of HCEs proceeding from hydrogen cyanide such that it can be recycled without any problem, i.e. without losses in reaction time, yield and quality, into a hydrogen cyanide preparation process.

BRIEF DESCRIPTION OF THE DRAWING

FIG. 1 is schematic of a reaction plant.

These problems, and further problems which have not been mentioned explicitly, are surprisingly solved by the inventive provision of a process for preparing HCEs proceeding from hydrogen cyanide, characterized in that ammonia formed in the step of alcoholysis of the corresponding alpha-hydroxycarboxamide, after a purification step, is recycled into the hydrogen cyanide preparation process (HCN process) still comprising at least one alkylamine. This solution is surprising in that the inventive purification step does not remove all the impurities from the ammonia formed from the alcoholysis reaction, especially alkylamines, and problem-free operation of an HCN process is nevertheless possible.

DETAILED DESCRIPTION OF THE INVENTION

Alpha-hydroxycarboxamides usable in the process according to the invention typically include all those carboxamides that bear at least one hydroxyl group in the alpha position to the carboxamide group.

Carboxamides in turn are common knowledge in the art. Typically, this is understood to mean compounds having groups of the formula —CONR'R"— in which R' and R" are each independently hydrogen or a group having 1-30 carbon atoms, which especially comprises 1-20, preferably 1-10 and especially 1-5 carbon atoms. The carboxamide may bear 1, 2, 3, 4 or more groups having the formula —CONR'R"—. These especially include compounds of the formula $R(—CONR'R")_n$ in which the R radical is a group having 1-30 carbon atoms, especially comprising 1-20, preferably 1-10, especially 1-5 and more preferably 2-3 carbon atoms, R' and R" are each as defined above and n is an integer in the range of 1-10, preferably 1-4 and more preferably 1 or 2.

The expression "group having 1 to 30 carbon atoms" denotes radicals of organic compounds having 1 to 30 carbon atoms. It includes not only aromatic and heteroaromatic groups but also aliphatic and heteroaliphatic groups, for example alkyl, cycloalkyl, alkoxy, cycloalkoxy, cycloalkylthio and alkenyl groups. These latter groups may be branched or unbranched.

According to the invention, aromatic groups are radicals of mono- or polycyclic aromatic compounds preferably comprising 6 to 20, more particularly 6 to 12, carbon atoms. Heteroaromatic groups are aryl radicals in which at least one CH group has been replaced by N and/or at least two adjacent CH groups have been replaced by S, NH or O.

Aromatic or heteroaromatic groups preferred in accordance with the invention derive from benzene, naphthalene, biphenyl, diphenyl ether, diphenylmethane, diphenyldimethylmethane, bisphenone, diphenyl sulphone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisooxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzoxathiadiazole, benzoxadiazole, benzopyridine, benzopyrazine, benzopyrazidine, benzopyrimidine, benzotriazine, indolizine, pyridopyridine, imidazopyrimidine, pyrazinopyrimidine, carbazole, acridine, phenazine, benzoquinoline, phenoxazine, phenothiazine, acridizine, benzopteridine, phenanthroline and phenanthrene, any of which may also optionally be substituted.

Preferred alkyl groups include methyl, ethyl, propyl, isopropyl, 1-butyl, 2-butyl, 2-methylpropyl, tert-butyl, pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and eicosyl.

Preferred cycloalkyl groups include cyclopropyl, cyclobutyl, cyclopentyl, cyclohexyl, cycloheptyl and cyclooctyl, any of which may optionally be substituted by branched or unbranched alkyl groups.

The preferred alkenyl groups include the vinyl, allyl, 2-methyl-2-propenyl, 2-butenyl, 2-pentenyl, 2-decenyl and 2-eicosenyl group.

The preferred heteroaliphatic groups include the aforementioned preferred alkyl and cycloalkyl radicals in which at least one carbon unit has been replaced by O, S or an $NR^8$ or $NR^8R^9$ group and $R^8$ and $R^9$ are each independently an alkyl group having 1 to 6 carbon atoms, an alkoxy group having 1 to 6 carbon atoms or an aryl group.

It is most preferable in accordance with the invention when the carboxamides bear branched or unbranched alkyl or alkoxy groups comprising 1 to 20 carbon atoms, preferably 1 to 12, advantageously 1 to 6 and in particular 1 to 4 carbon atoms and cycloalkyl or cycloalkyloxy groups comprising 3 to 20 carbon atoms, preferably 5 to 6 carbon atoms.

The radical R may bear substituents. The preferred substituents include halogens, especially fluorine, chlorine, bromine, and also alkoxy or hydroxyl radicals.

The alpha-hydroxycarboxamides may be used in the process of the invention individually or as a mixture of two or three or more different alpha-hydroxycarboxamides. Particularly preferred alpha-hydroxycarboxamides include alpha-hydroxyisobutyramide (HIBA) and/or alpha-hydroxypropionamide.

It is further of particular interest in one form of the process according to the invention to use those alpha-hydroxycarboxamides obtainable from ketones or aldehydes and hydrocyanic acid by cyanohydrin synthesis. The first step of said synthesis comprises reacting the carbonyl compound, for example a ketone, particularly acetone, or an aldehyde, for example acetaldehyde, propanal, butanal, with hydrocyanic acid to afford the particular cyanohydrin. It is particularly preferable when said synthesis comprises reacting acetone and/or acetaldehyde in typical fashion in the presence of a small amount of an alkali or an amine as catalyst. The cyanohydrin thus obtained is reacted with water in a further step to afford the alpha-hydroxycarboxamide.

Alcohols usable successfully in processes according to the invention include any alcohols familiar to those skilled in the art and also alcohol precursor compounds capable of undergoing an alcoholysis-type reaction with the HCA under the stated conditions of pressure and temperature. The reaction of the HCA is preferably carried out by alcoholysis with an alcohol preferably comprising 1-10 carbon atoms, more preferably comprising 1 to 5 carbon atoms. Preferred alcohols include, inter alia, methanol, ethanol, propanol, butanol, particularly n-butanol and 2-methyl-1-propanol, pentanol, hexanol, heptanol, 2-ethylhexanol, octanol, nonanol and decanol and mixtures thereof. It is particularly preferable when the alcohol used is methanol and/or ethanol, methanol being most advantageous. The use of precursors of an alcohol is also possible in principle. It is thus possible to use alkyl formates for example. Methyl formate or a mixture of methanol and carbon monoxide are particularly suitable.

In the context of the invention, it has been found that the procedure outlined can tolerate a broad spectrum of ratios of the reactants. Thus, the alcoholysis can be performed at a relatively high alcohol excess or deficiency relative to the HCA. Particular preference is given to process variants in which the conversion of the reactants is undertaken at a molar starting ratio of alcohol to HCA in the range from 1:3 to 20:1. Very particularly appropriately, the ratio is 1:2 to 15:1, and even more appropriately 1:1 to 10:1.

In one embodiment of the process according to the invention, the reaction between alpha-hydroxycarboxamide and alcohol is conducted in a pressure reactor. For this purpose, EP 2018362 and WO 2013/026603 are incorporated into the present application by reference for disclosure purposes.

The alcoholysis is conducted under a pressure of 1-100 bar. In addition, the pressure is greater than 1 bar during the separation/removal of the ammonia from the product mixture as well. More particularly, this means that the ammonia formed in the reaction is also distilled out of the mixture under a pressure of greater than 1 bar, completely dispensing with the use of auxiliaries such as stripping gas for distillative removal of the ammonia.

The product mixture, for the purposes of the invention, is depleted not just of ammonia but also of unconverted alcohol. Specifically in the case that methanol is used for alcoholysis, the result is a product mixture including ammonia and methanol components which are very difficult to separate from one another in principle. In the simplest case, for depletion of ammonia and alcohol from the product mixture, the two components are removed directly from the product mixture as a substance mixture. The two substances are then subjected to a downstream separating operation, for example a rectification. On the other hand, it is also possible for the purposes of the invention to separate the two alcohol (methanol) and ammonia components from the product mixture in one operation and, at the same time, also to separate the two ammonia and alcohol (methanol) constituents from one another.

In a preferred process modification of the invention, it may be of particular interest to spatially separate the reaction step and the removal of the ammonia/alcohol from the product mixture and to conduct them in different units. For this purpose, it is possible, for example, to provide one or more pressure reactors and combine them with a pressure distillation column. These are one or more reactors disposed in a separate region outside the column.

In the broadest sense, this means that reactant streams comprising an alpha-hydroxycarboxamide and an alcohol as reactants are fed into a pressure reactor, the reactant streams are catalytically reacted with one another in the pressure reactor at a pressure in the range of 1-100 bar, the resulting product mixture is discharged from the pressure reactor and the product mixture is depleted of alcohol and ammonia, with distillative removal of ammonia at a pressure which is kept constantly greater than 1 bar.

In a particular embodiment of this process variant, the conversion of the reactants and removal of ammonia/alcohol take place in two different spatially separate units. This has the advantage that different pressure ranges can be employed for the reaction/conversion of the reactants and the subsequent removal of ammonia/alcohol. Through the separation of the process into a conversion step in the pressure reactor under a higher pressure than in a separation step in a pressure column, both steps being conducted under elevated pressure, i.e. greater than 1 bar, it is possible to once again significantly improve the separating action and to increase the efficiency of the removal of the ammonia/alcohol mixture.

These quality features can be improved still further by repeating the reaction in the pressure reactor once or more than once with product mixture depleted of ammonia and alcohol the direction of the bottom of the separation column (pressure distillation column), with movement of the reaction step to a multitude of series-connected pressure reactors.

For the process variant specified, various temperature ranges have been found to be appropriate in the column and reactor. Thus, the pressure distillation column generally and preferably has a temperature in the range from about 50° C. to about 180° C. The exact temperature is typically established via the boiling system as a function of the pressure conditions that exist. The temperature in the reactor in the reaction of HIBA with methanol is preferably in the range of about 120-240° C.

As well as the variant described, in which the reaction of the alpha-hydroxycarboxamide with the alcohol from the removal of the resulting ammonia, inter alia, is conducted in two spatially separate but connected units, it may be preferable in a further process modification to undertake the conversion step and the removal step in a single unit. Pressure reactor and pressure distillation column are realized here in a single apparatus, and effectively coincide.

In a further variant of the process according to the invention, the HCE obtained is at least partly removed from the reaction mixture via the gas phase, preferably at least 60% by weight.

Accordingly, this variant is preferably executed in such a way that a maximum proportion of the product is converted to the gas phase. This aim can be achieved especially through the selection of the reactor, through the choice of pressure and temperature, and the gas volume in the operation of the reactor, especially in relation to the total volume or the liquid volume.

It is possible here to execute the reaction in such a way that the HCE is separated from the nitrogen compound released from the reaction mixture in a separate step. Advantages arise in embodiments which are characterized in that the HCE is removed from the reaction mixture preferably together with the ammonia released.

Further advantages arise especially through processes in which the molar ratio of HCE to ammonia during the removal of these components from the reaction mixture is in the range from 2:1 to 1:2. Of particular interest are processes in which the concentration of HCE in the liquid phase of the reaction mixture is preferably kept at less than 30% by weight. Preferably, the molar ratio of HCE to alpha-hydroxycarboxamide in the liquid phase of the reaction mixture is less than 1.

Additional advantages with regard to the productivity of the process can be achieved by introducing the alcohol into the reaction mixture as a gas. The type of reactor for performance of the present process is not restricted. Preference is given, however, to using those reactors where relatively large gas volumes can be introduced or discharged. Preference is accordingly given to using multiphase reactors for performance of this process variant. It is possible here to use multiphase reactors in which a gas is introduced in countercurrent relative to the liquid phase. These reactors include reactors based on sparged stirred tanks or cascades. In addition, the alcohol can be passed in gaseous form through a tray column or column having random packings, in countercurrent to the liquid.

In a preferred embodiment, the alcohol can be introduced into the reaction mixture in cocurrent. Particularly suitable reactors for this purpose include trickle bed reactors, bubble column reactors, jet scrubbers and falling-film reactors, particular preference being given to trickle bed reactors and falling-film reactors or to the combination of trickle bed reactors and falling-film reactors.

The conversion according to the invention takes place in the presence of a catalyst. These include homogeneous catalysts and heterogeneous catalysts.

Illustrative homogeneous catalysts for the performance of the process according to the invention are water-resistant lanthanoid compounds. Lanthanoid compounds refer to compounds from the group of the lanthanoids, such as La, Ce, Pr, Nd, Pm, Sm, Eu, Gd, Td, Dy, Ho, Er, Tm, Yb and/or Lu. Preference is given to using a lanthanoid compound comprising lanthanum.

Preferably, the lanthanoid compound has a solubility in water of at least 1 g/l, preferably at least 10 g/l, at 25° C.

Preferred lanthanoid compounds are salts which are preferably in the oxidation state of 3.

As well as the preferred variants of homogeneous catalysis, processes employing heterogeneous catalysts are also appropriate. Successfully usable heterogeneous catalysts include magnesium oxide, calcium oxide and basic ion exchangers, and further similar examples.

For example, preferred processes may be those in which the catalyst is an insoluble metal oxide containing at least one element selected from the group consisting of Sb, Sc, V, La, Ce, Ti, Zr, Hf, V, Nb, Ta, Cr, Mo, W, Tc, Re, Fe, Co, Ni, Cu, Al, Si, Sn, Pb and Bi.

Alternatively, preferred processes may be those wherein the catalyst used is an insoluble metal selected from the group consisting of Ti, Zr, Hf, V, Nb, Ta, Cr, Mo, W, Fe, Co, Ni, Cu, Ga, In, Bi and Te.

The preferred heterogeneous catalysts especially include catalysts based on $ZrO_2$ and/or $Al_2O_3$. Particularly preferred catalysts of this generic type are described in detail especially in JP 6-345692, the catalysts detailed in the publication JP 06-345692 being incorporated into the present application by reference for disclosure purposes.

Further suitable catalysts are described in DE 102013213699, filed at the GPTMO on Dec. 7, 2013. This publication is incorporated into the present application by reference for disclosure purposes.

Particular preference is given therein to catalysts based on $ZrO_2$ and $Al_2O_3$, with very particular preference for use of lanthanum oxide-, silicon oxide- or yttrium oxide-doped $ZrO_2$ catalysts. The latter are commercially available, for example, as zirconium oxide catalyst SZ 61157 from Saint-Gobain Nopro. The yttrium incorporated in the zirconium oxide crystal lattice brings about stabilization of the tetragonal phase of zirconium oxide, which is otherwise stable only above 1200° C., even at room temperature. In industry, they are used as oxygen conductors for solid oxide fuel cells or in oxygen measuring instruments (A probe). A composition with 8 mol % of $Y_2O_3$ is typical here. In the process according to the invention, lanthanum oxide, silicon oxide or yttrium oxide contents based on $ZrO_2$ of 0.05-20 mol %, preferably of 0.5-15 mol %, more preferably 1-10 mol % and most preferably 2-5 mol % are used. It is also possible to use mixtures of the catalysts mentioned.

When $Al_2O_3$ is used, doping with BaO has been found to be useful. Good results are achieved with 0.01-1.2 mol % of BaO based on $Al_2O_3$. Particular preference is given to 0.05-1.0 mol %, very particular preference to 0.1-0.8 mol %.

It has been found that, surprisingly, these catalysts have a high tolerance to the presence of water. Thus, in the alcoholysis reaction, the water content in the reactant feed may be 0.1-20 mol %. Preference is given to 0.5-10 mol %, particular preference to 1-3 mol %.

The reaction temperature may vary over a wide range, and the reaction rate generally increases with increasing temperature. The upper temperature limit generally results from the boiling point of the alcohol used. Preferably, the reaction temperature is in the range of 40-300° C., more preferably of 120-240° C.

In a further variant of the process according to the invention, the alcoholysis can be effected in the gas phase. An illustrative gas phase variant which is hereby disclosed but does not limit the process according to the invention is EP 2415750.

This describes a gas phase process which in the presence of a zirconium dioxide catalyst at temperatures of 150-270° C. and pressures of 1-300 kPa, where the zirconium dioxide catalyst may also contain elements such as B, Al, Mn, Co, Ni, Y, La or Yb or mixtures thereof.

This gas phase process is conducted with the heterogeneous catalysts mentioned in a fixed bed or fluidized bed reactor. The reaction here proceeds in the gas phase in principle, the proportion of the liquid phase being 10% by weight or less, based on the total amount of the feedstocks.

Alcohol and HCA may be evaporated before being metered into the reactor or evaporated in the reactor itself. In addition, alcohol and HCA may be fed to the reactor separately or in already mixed form. Preference is given to a variant wherein the reaction proceeds under inert gas, preferably nitrogen, which allows easier evaporation because of the reduced partial pressure of the reaction components.

When the reaction components are evaporated in the reactor, they can be metered into the reactor together with a solvent. Possible solvents are, for example, ether-based solvents such as tetrahydrofuran, amide-based solvents such as N-methylpyrrolidone, or ester-based solvents such as methyl lactate, or the like. For this variant, however, preference is given to a solvent-free execution of the gas phase reaction.

The reaction temperature is correspondingly chosen such that the reaction components are present in the reactor in sufficiently evaporated form. This depends on the nature of the amide or alcohol, the molar ratio thereof, and the presence of an inert gas or solvent. For sufficient evaporation of HIBA, a reaction temperature of >150° C. is chosen, and in the case of reaction under atmospheric pressure a reaction temperature of >180° C. If the reaction temperature is kept <240° C., the breakdown of HIBA to acetone, or the formation of by-products such as alpha-alkoxyisobutyric acid or of olefin derivatives which form through dehydrogenation, is avoided.

To obtain a conversion rate which is stable over a long period, the metering rate is 0.01-5 parts by weight/h of HCA, based on the amount of catalyst used. Preferably, the WHSV (weight hourly space velocity) based on the alcohol reaction component is 0.01-100 $h^{-1}$.

For discharge of the desired HCE and for the separation thereof from ammonia, by-products formed and starting materials unconverted, it is possible in this process variant to use standard separation processes, for example distillation.

A further gas phase process variant according to the invention is conducted in the presence of water. It has been found that, surprisingly, for example in the case of reaction of HIBA with methanol in the presence of water, the formation of by-products, especially acetone or 2-amino-2-methylpropionitrile (AMPN), are suppressed very significantly, and the selectivity for MHIB and the catalyst service life are substantially increased. Water can either be added to the reactant feed or fed directly into the reactor. The molar ratio of water to HCA is 0.1-10, preferably 0.3-5 and more preferably 0.5-1 mol/mol.

The molar ratio of alcohol to HCA in this variant is 1-25, preferably 3-20 and more preferably 5-9 mol/mol.

The alcoholysis of the HCA gives rise to numerous by-products, especially alkylamines and olefins, which are difficult to separate from the ammonia reaction product. If the alcoholysis, in the preferred variant, is effected with the HIBA and methanol reaction components, this methanolysis forms, as by-products, dimethoxypropane, methoxypropene, methyl formate, methyl acetate, dimethylisopropylamine, propylene and especially dimethylamine and trimethylamine.

If this ammonia of reaction, after the separation from the unconverted alcohol, is fed as starting material directly into an HCN process, for example into an Andrussow process, there is a significant drop in catalyst activity after only a very short time, within a few minutes, which is noticeable by a distinct rise in the temperature at the catalyst mesh.

It has now been found that, surprisingly, in the case of intermediate connection of a purification step including solid adsorbents, this drop in catalyst activity can be avoided, even though at least an alkylamine is still present in the ammonia fed into the HCN process. In this case, the concentration of the alkylamine impurity, based on ammonia, may be 0.1-10%, preferably 0.2-8% and more preferably 0.5-6% by weight.

Useful solid adsorbents for the purification step according to the invention are preferably activated carbons.

Activated carbon can be used in all possible morphological forms, in powder form, in granulated form, or as cylindrical or spherical pellets. Preference is given to granulated and pelletized activated carbons having surface values of 1000-1500 $m^2/g$, more preferably 1200-1400 $m^2/g$. As well as activated carbon activated chemically with zinc chloride or phosphoric acid, activated carbons which have been gas-activated using alkali metal salts, alkali metals, chlorides, sulphates and acetates are preferred.

Particularly suitable activated carbons are the following commercially available products from Donau Carbon: Hydraffin CC 12×40, Alcarbon DC 60/8×16 or Supersorbon C IV.

Possible inventive adsorbers are fixed bed, moving bed or fluidized bed adsorbers, preference being given to the former. Illustrative apparatus solutions are described, for example, in Ullmann's Encyclopedia of Industrial Chemistry, Wiley 2012, p 555 ff. (DOI: 10.1002/14356007.b03_09.pub2). The procedure can be effected continuously or batchwise, preference being given to the former.

The adsorption is conducted within a temperature range of 0-150° C., preferably of 30-100° C., more preferably of 60-80° C., and at pressures of 0.05-5 bar, preferably at 0.2-4 bar, more preferably at 1-3.5 bar.

The ammonia purified in accordance with the invention can thus be used as reactant without any problem in various HCN processes or other preparation processes. For example, the reaction of ammonia with methanol to give HCN is detailed in EP 0941984. In addition, HCN can be obtained from ammonia and methane by the BMA or Andrussow process, these processes being described in Ullmann's Encyclopedia of Industrial Chemistry 5th edition on CD-ROM, under "Inorganic Cyano Compounds". It is likewise possible to recycle ammonia, for example, into an ammoxidation process, for example the industrial scale synthesis of acrylonitrile from ammonia, oxygen and propene. Acrylonitrile synthesis is described, for example, under "Sohio process" in Industrial Organic Chemistry by K. Weissermel and H.-J. Arpe on pages 307 ff.

The examples which follow are intended to illustrate the process according to the invention but not limit it in any way.

EXAMPLES

The examples and comparative examples were conducted in a plant as shown in FIG. 1. Through the three metering lines 1, 2 and 3, ammonia, air and methane were introduced into the pilot plant. Ammonia can be fed to the static mixer (B) by means of the two three-way valves (DW) either directly or via an adsorber bed (A) filled with activated carbon. The adsorber bed is heatable. The reactants are mixed in a static mixer and then fed via line 8 to the preheater (C), preheated to the desired temperature and introduced via line 9 into the reactor (R). The latter is equipped with a catalyst mesh (D) and an air cooler (E); the product gas mixture is cooled to a desired temperature in the latter. This product gas mixture is then sent partially to an online analysis via line 12, and partially to a combustion via line 11, since no storage of the HCN formed is intended in the case of the experiment.

LIST OF DESIGNATIONS

1: ammonia inlet
2: air inlet
3: methane inlet
4: bypass line for adsorber bed
5: adsorber inlet
6: adsorber outlet
7: static mixer inlet
8: preheater inlet
9: Andrussow reactor inlet
10: Andrussow reactor outlet
11: partial discharge of product mixture
12: online analysis inlet
13: online analysis outlet
14: overall product mixture outlet
A: adsorber bed
B: static mixer
C: preheater
D: catalyst mesh
E: air cooler
F: online analysis
R: reactor

COMPARATIVE EXAMPLES 1-2,

Example 1

These are conducted in a plant analogous to FIG. 1. In Comparative Example 1, pure ammonia is used; in Comparative Example 2, 34% by weight of ammonia of reaction from the HIBA alcoholysis and a catalyst are added thereto. In both cases, the ammonia feed is not conducted through the adsorber bed. In Inventive Example 1, Comparative Example 2 is repeated, except that the entire ammonia feed is passed through the adsorber bed, which is filled with Hydrafin CC 12×40 activated carbon. The results are shown in Tab.1 for Comparative Example 1 and Example 1 after a TOS (time on stream) of 14 d and, for Comparative Example 2, after a TOS of 1 h. Likewise shown are the amine impurities in the ammonia of reaction prior to introduction into the adsorber bed.

TABLE 1

Influence of activated carbon

|  | Comparative Example 1 | Comparative Example 2 | Example 1 |
|---|---|---|---|
| Ammonia (99.9%)/g/min | 2.506 | 0.906 | 0.799 |
| Ammonia of reaction/g/min | 0 | 1.600 | 1.600 |
| $NH_3$ (% by wt.) | 92.0 | | |
| MeOH (% by wt.) | 1.5 | | |
| TMA (% by wt.) | 5.5 | | |
| DME (% by wt.) | 1.0 | | |
| Methane (Linde 3.8) (g/min) | 2.25 | 2.096 | 1.95 |
| Air (g/min) | 21.82 | 19.74 | 19.90 |

TABLE 1-continued

Influence of activated carbon

|  | Comparative Example 1 | Comparative Example 2 | Example 1 |
|---|---|---|---|
| N total/C total (mol/mol) | 1.049 | 1.034 | 1.032 |
| $NH_3/CH_4$ (l/l) | 1.049 | 1.069 | 1.080 |
| Air/($NH_3 + CH_4$) (l/l) | 2.63 | 2.51 | 2.72 |
| $HCN/NH_3$ yield (mol %) | 63 | 13 | 65 |

The yield of HCN is significantly increased with activated carbon-purified ammonia feed containing ammonia of reaction compared to unpurified, and is comparable to pure ammonia.

Examples 2-4

Example 1 was repeated, and the adsorption was conducted at different adsorber bed temperatures. The activated carbon used was Alcarbon PH 55×8C from Donau Carbon. The results are shown in Tab. 2.

TABLE 2

Temperature dependence

|  | Example 2 | Example 3 | Example 4 |
|---|---|---|---|
| Adsorber bed temperature (° C.) | 20° C. | 70° C. | 100° C. |
| $NH_3$ (% by wt.) | 95.783 | 95.084 | 95.084 |
| TMA (% by wt.) | 2.097 | 2.512 | 2.512 |
| DME (% by wt.) | 0.792 | 0.753 | 0.753 |
| MeOH (% by wt.) | 1.328 | 1.65 | 1.65 |
| $HCN/NH_3$ yield mol % | 63.26 | 62.57 | 62.51 |

Treatment with activated carbon achieves good results in terms of HCN yield over a wide temperature range.

The invention claimed is:

1. A process for preparing an alpha-hydroxycarboxylic ester, comprising:
    preparing hydrogen cyanide,
    alcoholysis of an alpha-hydroxycarboxamide to obtain said alpha-hydroxycarboxylic ester,
    wherein ammonia and at least one alkylamine formed in the alcoholysis of the alpha-hydroxycarboxamide, after a purification step, are recycled into the hydrogen cyanide preparation process still comprising at least one alkylamine
    wherein the hydrogen cyanide preparation is according to an Andrussow process of reaction of methane with ammonia.

2. The process according to claim 1, wherein a concentration of a total amount of the alkylamines based on ammonia is 1-100 000 ppm.

3. The process according to claim 1, wherein the alpha-hydroxycarboxylic ester is methyl 2-hydroxyisobutyrate.

4. The process according to claim 1, wherein the alkylamine is trimethylamine.

5. The process according to claim 1, wherein the ammonia is purified by an absorbent by passage through a solid.

6. The process according to claim 1, wherein the ammonia is purified in a continuously operated adsorber bed.

7. The process according to claim 1, wherein the ammonia is purified by activated carbon.

8. The process according to claim 1, wherein the alcoholysis reaction of the alpha-hydroxycarboxamide is effected in a liquid phase or in a gas phase.

9. The process according to claim 1, wherein the purification is effected within a temperature range from 0° C. to 150° C.

10. The process according to claim 1 wherein the purification is effected within a pressure range from 0.05 to 5 bar.

11. The process according to claim 1, comprising:
   a) feeding a reactant stream comprising the alpha-hydroxycarboxamide and an alcohol into a pressure reactor containing a catalyst, to obtain a reaction mixture,
   b) converting the reaction mixture in the pressure reactor at a pressure in the range of 0.1-100 bar, to obtain a product mixture,
   c) depleting the product mixture of alcohol and ammonia that arises from b),
   d) separating alcohol and ammonia containing at least trimethylamine and
   e) purifying ammonia containing at least trimethylamine by activated carbon before said ammonia into the hydrogen cyanide preparation process.

* * * * *